United States Patent [19]

Kraus

[11] Patent Number: 4,611,597

[45] Date of Patent: Sep. 16, 1986

[54] IMPLANTABLE DEVICE FOR THE STIMULATION OF BONE GROWTH

[76] Inventor: Werner Kraus, Augustenstr. 41 Rgb., Munich, Fed. Rep. of Germany

[21] Appl. No.: 547,950

[22] Filed: Nov. 2, 1983

[30] Foreign Application Priority Data

Nov. 3, 1982 [DE] Fed. Rep. of Germany ....... 3240592

[51] Int. Cl.$^4$ .............................................. A61N 1/32
[52] U.S. Cl. .................................. 128/419 F; 128/784
[58] Field of Search ..................... 128/419 F, 424, 784, 128/785, 82.1, 783

[56] References Cited

U.S. PATENT DOCUMENTS

| 3,745,995 | 7/1973 | Kraus | 128/419 F |
| 3,820,534 | 6/1974 | Kraus | 128/82.1 |
| 3,918,440 | 11/1975 | Kraus | 128/419 F |
| 3,968,790 | 7/1976 | Fukada et al. | 128/419 F |
| 4,306,564 | 12/1981 | Kraus | 128/419 F |
| 4,421,115 | 12/1983 | Kraus | 128/419 F |

Primary Examiner—William E. Kamm
Attorney, Agent, or Firm—Frishauf, Holtz, Goodman & Woodward

[57] ABSTRACT

An implantable device for the stimulation of bone growth, the device having an elongated pickup coil arrangement that is provided with connectors for tissue electrodes. An extended and strip-like tissue electrode extends from the pickup coil arrangement and the connectors have a hole for a bone screw and a sleeve-like extension adapted to accommodate a Kirschner wire electrode.

5 Claims, 7 Drawing Figures

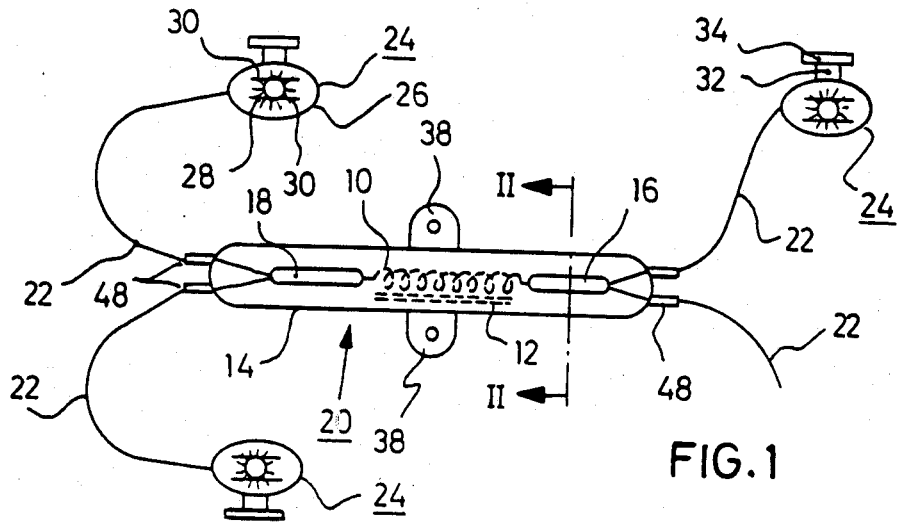
FIG. 1
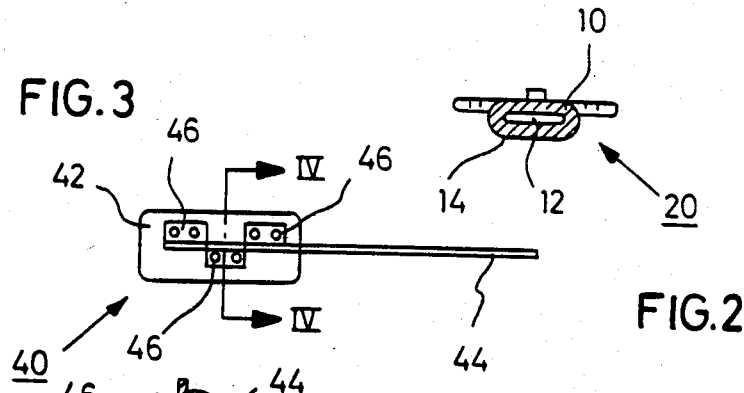
FIG. 3
FIG. 2
FIG. 4
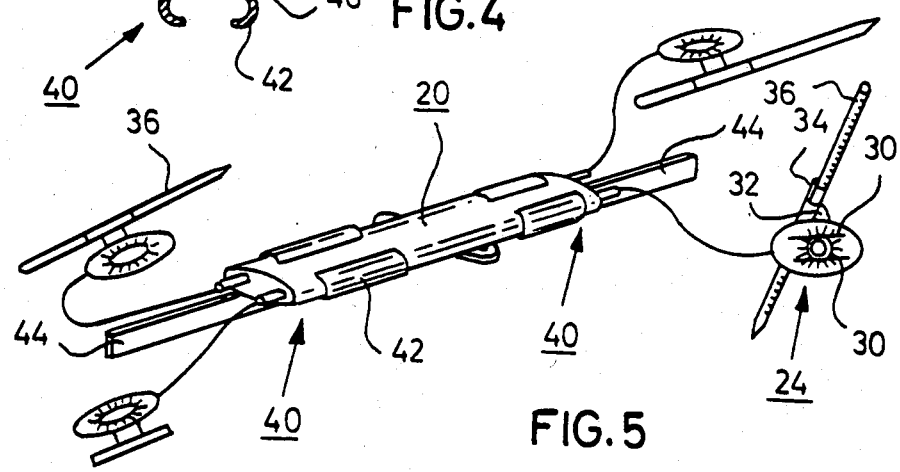
FIG. 5

IMPLANTABLE DEVICE FOR THE STIMULATION OF BONE GROWTH

The present invention relates to an implantable device for the stimulation of bone growth, generally of the type disclosed in U.S. Pat. No. 3,918,440. In particular, the present invention relates to a device for healing bone damage by means of low frequency electric current which is generated by means of induction and which is preferably of a frequency below 30 Hz.

THE INVENTION

The present invention provides an improved device of the type described above which is more versatile and more comfortable and in particular is suitable for healing major bone defects (e.g., diastases of up to 10 centimeters or more).

According to the present invention, there is provided an implantable device for the stimulation of bone growth having a pickup coil arrangement which comprises a pickup coil, at least a first and a second electrical connector, and a cover of tissue-compatible material that is elongated and surrounds the pickup coil; at least one connector device for connection to a tissue electrode, which connector device is connected electrically by means of an insulated wire with one end of the pickup coil; and at least one electrode arrangement which comprises: an extended strip-like tissue electrode which is connected with the other end of the pickup coil, the strip-like tissue electrode extending in the longitudinal direction of the cover, and substantially perpendicular to the cover.

In the present device bone screws and/or Kirschner wires and/or easily attachable strip-like electrodes ("keel electrodes") are used as electrodes, according to choice. The electrode structure for the application of the low frequency alternating current that is induced by the low frequency electromagnetic field can thus be very well matched to any particular situation.

DRAWINGS

A preferred exemplary version of the invention is described below with reference to the accompanying drawings appended hereto, in which:

FIG. 1 is a simplified schematic plan view of a device according to one exemplary version of the invention;

FIG. 2 is a cross section taken on line II—II of FIG. 1;

FIG. 3 is a plan view of a strip-like electrode ("keel electrode") that can be slid into position;

FIG. 4 is a cross section taken on line IV—IV of FIG. 3;

FIG. 5 is a perspective view of a device according to FIG. 1 with the keel electrode positioned according to FIGS. 3 and 4, as well as with additional Kirschner wire electrodes;

DETAILED DESCRIPTION

Figures 6, 7:
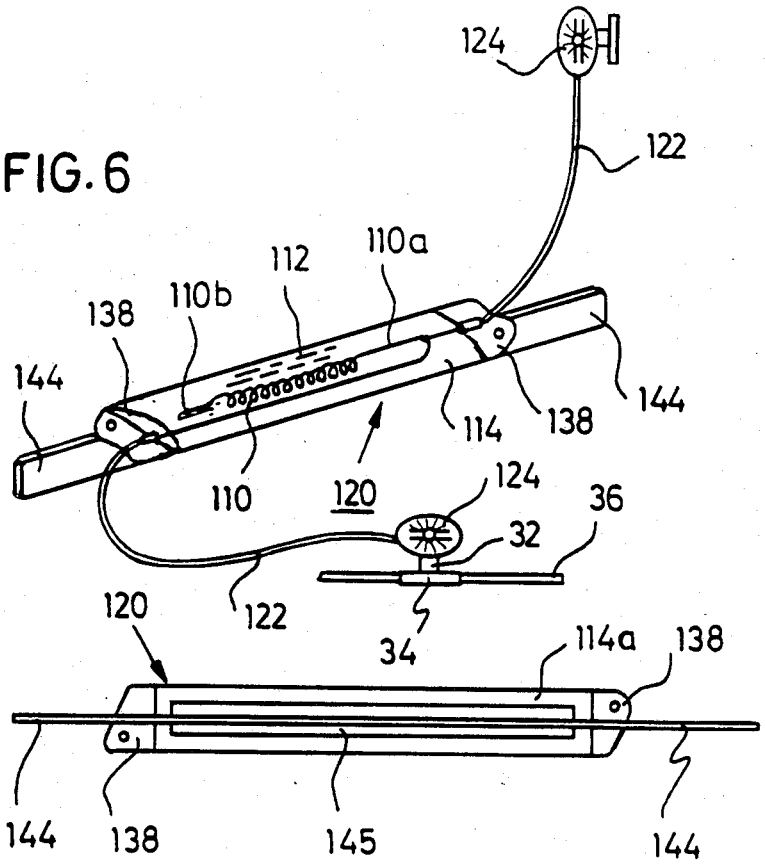
FIG. 6 is a perspective view of a preferred embodiment of the invention.
FIG. 7 is a plan view of the underside of the device according to FIG. 6.

FIGS. 1 to 5 show an implantable device which comprises: a solenoid-like pickup coil 10 having a magnetic core 12, that is shown in FIG. 1 as a circuit diagram. The pickup coil 10 and the magnetic core 12 are surrounded by a cover 14 made of a tissue compatible insulating material, e.g. polytetrafluoroethylene (PTFE). The pickup coil 10, core 12 and cover 14 form together a pickup coil arrangement designated by numeral 20 in FIG. 1.

The ends of the pickup coil 10 are connected electrically in each instance with elongated contacts 16 and 18 respectively, which are arranged with their surfaces lying freely on one side of the pickup coil arrangement 20 along the longitudinal axis of the pickup coil arrangement, as can be seen from FIG. 1. The ends of the elongated contacts 16 and 18 are in each instance connected with two insulated connector wires 22 that in each instance lead to a connector device 24. The connector devices 24 consist of a tissue-compatible electrically conductive material, such as osteosynthesis metal, and comprise an elongated, plate-like portion 26 having a hole 28 for a bone screw. The area that surrounds the hole is dished, in order to accept the head of the screw, and in addition on the diametrically opposite sides of the hole 28 there are two tangentially parallel slots 30 provided so that bone screws of different thicknesses can be inserted. The connector devices 24 also have in each instance a lateral tab 32 which connects the portion 26 to a sleeve-like rolled part 34. The sleeve-like part 34 is adapted to accommodate a Kirschner wire 36 shown in FIG. 5.

The cover 14 is provided with lateral, pierced, tab-like portions 38 which enables the pickup coil arrangement 20 to be fixed in the implantation area by means of a wire or the like.

The contacts 16 and 18 serve to provide respective electrical connections for electrode arrangements 40, one of which is shown in FIGS. 3 and 4. Each electrode arrangement 40 comprises a clamp-like part 42, that matches the cross sectional shape of the pickup coil arrangement 20, and a strip-like electrode 44. The electrode 44 is connected to the clamp-like part 42 by means of tab-like extensions 46 which may be spot welded into place. The electrode arrangements 40 can be slid in a longitudinal direction onto the pickup coil arrangement 20 in such a manner that the contacts 16 and 18, respectively, produce electrical connections between the pickup coil 10 and the clamp-like portions 42 and the strip-like electrodes 44 ("keel electrodes"). When the electrode arrangements 40 are installed on the one side of the pickup coil arrangement 20, the strip-like electrodes 44 run axially with respect to the pickup coil arrangement and project beyond its ends as can be seen in FIG. 5. The strip-like electrodes 44 form tissue electrodes which in the installed state extend in the main perpendicularly from the cover 14 and thus stand "on edge" on the relevant part of the outside of the cover 14.

The cover 14 can be provided with peg-like extensions 48 where the insulated connector wires 22 emerge which will serve to prevent the wires from becoming kinked.

When this device is used, it is implanted in the area of the bone damage that is to be repaired. Even major diastases can be bridged by means of the strip-like electrodes 44. According to need, any number of connector devices 24 can be provided with bone screw electrodes and/or Kirschner electrodes. The tabs 32 consist of a relatively thin sheet of metal that can be very easily bent and twisted so that the inserted Kirschner wires 36 can be implanted and oriented as desired, as can be seen, for example, in the lower right hand part of FIG. 5.

The strip-like electrodes 44 can be cut to any desired length. In addition, they can be bent should this be desired. Insofar as the connector devices 24 are not needed, they can, together with the associated connector wire on the extensions 48, simply be cut off.

Because of the slots 30 the connector devices can be used for screws of various diameters, e.g., screws with diameters between 3.0 and 4.5 mm can be used. The sleeve-like part 34 normally has an internal diameter of approximately 2 mm, but since it is not closed, it can also accommodate thicker Kirschner wires. The pickup coil 10 and the magnetic core 12 can be configured in any familiar manner. After implantation, a low frequency alternating current is induced in the pickup coil 10 in the above described device.

The pickup coil arrangement 20 can in practice have a cross section in the form of a flat rectangle having rounded corners, the longer side of which is approximately 12 mm and the shorter side of which is approximately 6 mm. The length of the pickup coil arrangement 20 without the connecting wires can amount to approximately 75 mm. The strip-like electrodes 44, which, as shown, stand preferably perpendicularly on the flat side of the pickup coil arrangement, can be approximately 60 to 80 mm long, approximately 4 to 7 mm wide, and approximately 0.5 mm thick. The electrode arrangements 40 consist preferably of a tissue compatible osteosynthesis metal, such as a conventional cobalt-chromium alloy.

The preferred embodiment of the implantable device according to the invention is shown schematically in FIGS. 6 and 7 and comprises a pickup coil arrangement 120, which is in the main configured like the pickup coil arrangement 20 according to FIG. 1. The pickup coil arrangement 120 comprises a pickup coil 110, a magnetic core 112 as well as a cover 114. The cover is provided with securing tabs 138 at its longitudinal ends. In this embodiment, all the connector devices 124 are connected by insulated wires 122 to the same connector 110a. Connector 110b is connected permanently to a continuous and strip-like planar tissue electrode 144 which in turn is connected permanently to the pickup coil arrangement 120 and extends in a longitudinal direction from the pickup coil arrangement 120. The electrode 114 stands on edge upon the pickup coil arrangement 120 and extends longitudinally beyond the ends of the pickup coil arrangement as can be seen particularly in FIG. 7. The pickup coil arrangement 120 has a peripheral surface with a flattened underside 114a, upon which there is an additional plate-like electrode 145, which is connected electrically and mechanically with the keel-like tissue electrode 144 and which forms an additional contact surface on the cover of the underside of the pickup coil arrangement 120.

The keel-like tissue electrode 144 is mechanically and rigidly connected to the pickup coil arrangement 120 and the additional plate-like electrode 145 thereby forming one electrode, and the connector devices 124, with the electrodes which are attached to them, such as a Kirschner wire 36 or a bone screw (not shown), form the opposite pole. The strip-like electrode 144 can in practice be 120 mm long and when used can be cut to the length required to bridge a bone defect.

The embodiment shown in FIGS. 6 and 7 can be changed in that the electrode combination 144 and 145 can be divided transverse to the longitudinal direction of the arrangement 120 into two electrically separate parts, and each part would contain similar tissue electrodes which stand on edge as in FIG. 5 and project beyond one end of the arrangement 120. The two parts of the electrode combination are then connected by means of different connectors to the pickup coil 110. The portion of the strip-like electrode 144 and the connector wire 122 for the connector device 124 which are located at the same axial end of the device 120 are then preferably connected to different connectors of the pickup coil.

The plate-like electrode 145 which forms the additional contact surface is preferably mechanically connected rigidly to the strip-like tissue electrode 144 and assists in anchoring electrode 144 to the arrangement 120.

I claim:

1. An implantable device, for the stimulation of bone growth, having
   a pickup coil arrangement (120) including
   a pickup coil (10, 110) and at least a first and a second connection (16, 18; 110a, 110b) therefor, and an elongated cover (14, 114) having a peripheral surface and a pair of opposing end surfaces, of a tissue-compatible material, surrounding the pickup coil (10, 110); and
   first and second electrical conduction means (22, 122; 24, 124) establishing first and second tissue connections;
   wherein said first conduction means comprises
   a tissue electrode, including an extended, strip-like, planar tissue electrode element (44, 144), coupled to and extending longitudinally along the cover (14, 114), and projecting edgewise substantially perpendicular to said peripheral surface thereof, said tissue electrode being coupled to one (18, 110b) of the connections (16, 18; 110a, 110b) of the pickup coil;
   said second conduction means comprises at least one connector device (124) coupled to the other (16; 110a) of the connections (16, 18; 110a, 110b) of the pickup coil; and
   a flexible insulated wire (122) is provided, interconnecting each connector device (124) and said other connection (16; 110a) of the pickup coil.

2. A device according to claim 1, characterized in that the extended tissue electrode (44, 144) extends beyond the longitudinal ends of the cover.

3. A device according to claim 1, characterized in that the the cover is approximately in the form of a flat rectangle and in that the plane of the strip-like tissue electrode (44, 144) extends perpendicularly to the larger side of the rectangle.

4. A device according to claim 3, characterized in that the extended tissue electrode (44, 144) extends beyond the longitudinal ends of the cover.

5. A device according to claim 1, characterized by a plate-shaped electrode (145) formed on the surface of the cover (14, 114), the strip-like electrode element (44, 144) projecting from said plate-shaped electrode (145) and being electrically connected thereto.

* * * * *